US00PP28465P3

(12) United States Plant Patent
Giesen

(10) Patent No.: US PP28,465 P3
(45) Date of Patent: Sep. 26, 2017

(54) ***LOBELIA* PLANT NAMED 'LOBZ0010'**

(50) Latin Name: ***Lobelia erinus* L.**
Varietal Denomination: LOBZ0010

(71) Applicant: SYNGENTA PARTICIPATIONS AG, Basel (CH)

(72) Inventor: Eric Giesen, Andijk (NL)

(73) Assignee: Syngenta Participations AG, Basel (CH)

( * ) Notice: Subject to any disclaimer, the term of this patent is extended or adjusted under 35 U.S.C. 154(b) by 91 days.

(21) Appl. No.: 14/756,551

(22) Filed: Sep. 16, 2015

(65) Prior Publication Data

US 2017/0013766 P1 Jan. 12, 2017

(30) Foreign Application Priority Data

Jul. 7, 2015 (QZ) ..... PBR 2015/1566

(51) Int. Cl.
*A01H 5/02* (2006.01)

(52) U.S. Cl.
USPC ..... Plt./451

(58) Field of Classification Search
USPC ..... Plt./451
See application file for complete search history.

(56) References Cited

PUBLICATIONS

UPOV hit on *Lobelia* plant named 'LOBZ0010', QZ PBR 20151566, application date Jul. 7, 2015.*

* cited by examiner

*Primary Examiner* — Anne Grunberg
(74) *Attorney, Agent, or Firm* — Dale Skalla

(57) ABSTRACT

A new *Lobelia* plant named 'LOBZ0010' particularly distinguished by large, white flowers, strong stems with long inflorescences, medium green foliage, narrow leaves, medium sized, free branching, tight, mounding plant habit with upright directed stems.

1 Drawing Sheet

Latin name of the genus and species of the plant claimed: *Lobelia erinus* L.

Varietal denomination: 'LOBZ0010'.

BACKGROUND OF THE NEW PLANT

The present invention comprises a new and distinct cultivar of *Lobelia*, botanically known as *Lobelia erinus*, and hereinafter referred to by the cultivar name 'LOBZ0010'.

'LOBZ0010' is a product of a planned breeding program. The new cultivar has large, white flowers, strong stems with long inflorescences, medium green foliage, narrow leaves, free branching, and a medium sized, tight and upright plant habit.

'LOBZ0010' originated from a hybridization made in May 2010 in Andijk, The Netherlands. The female parent was an unpatented, proprietary *Lobelia* plant designated 'LOB09-418-2', having smaller flowers, lighter green leaves and a trailing plant habit, while plant habit of 'LOBZ0010' is distinctly more upright.

The male parent of 'LOBZ0010' was the proprietary *Lobelia* plant designated 'LOB09-418-3' (unpatented), having white flowers, more gray and hairy foliage, and longer stems than 'LOBZ0010'.

The resulting seeds were sown in June 2010 and 'LOBZ0010' was selected as one flowering plant within the progeny of the stated cross in September 2010 in a controlled environment in Andijk, The Netherlands.

The first act of asexual reproduction of 'LOBZ0010' was accomplished when vegetative cuttings were propagated from the initial selection in the summer of 2011 in a controlled environment in Andijk, The Netherlands.

BRIEF SUMMARY OF THE INVENTION

Horticultural examination of plants grown from cuttings of the plant initiated in the spring of 2014 in Andijk, The Netherlands, and continuing thereafter, has demonstrated that the combination of characteristics as herein disclosed for 'LOBZ0010' are firmly fixed and are retained through successive generations of asexual reproduction.

'LOBZ0010' has not been observed under all possible environmental conditions. The phenotype may vary significantly with variations in environment such as temperature, light intensity and day length.

A Plant Breeder's Right for this cultivar was applied for with the European Union Office (CPVO) on Jul. 7, 2015, No. 2015/1566.

The following traits have been repeatedly observed and are determined to be basic characteristics of the new variety. The combination of these characteristics distinguishes this *Lobelia* as a new and distinct variety.

DESCRIPTION OF THE PHOTOGRAPHS

Figure 1:
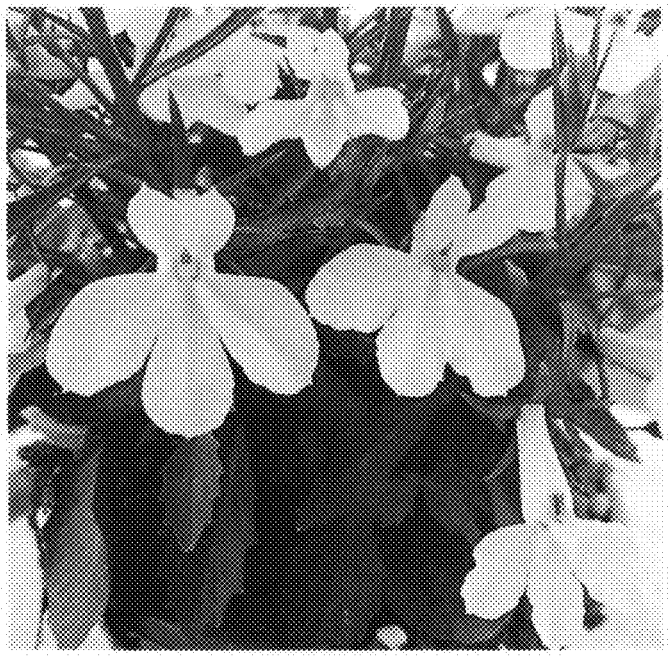
Figure 2:
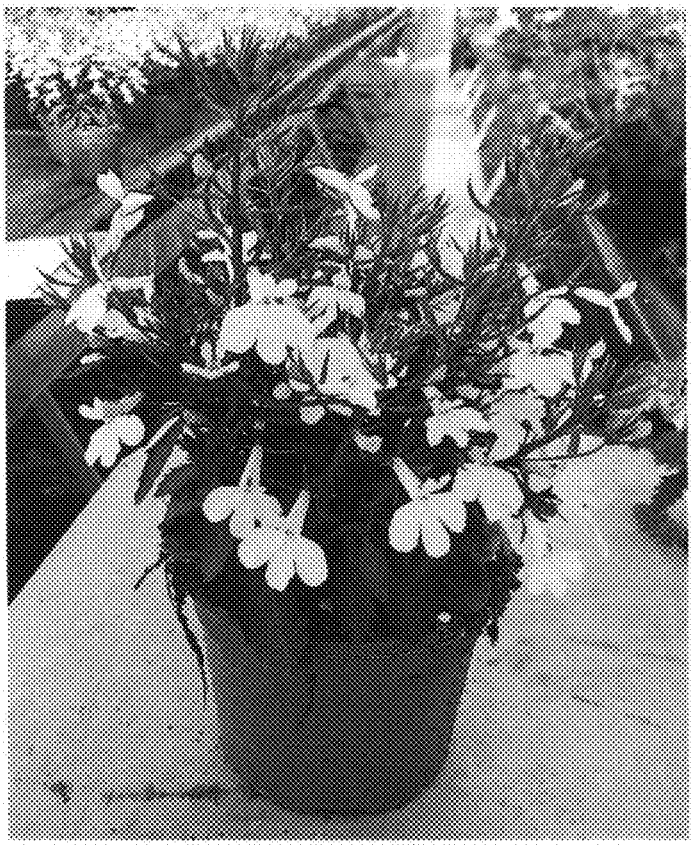

The accompanying photographic drawings show typical flower and foliage characteristics of 'LOBZ0010' with colors being as true as possible with an illustration of this type. The photographic drawings show in FIG. 1 a close-up of the flowers and in FIG. 2 a flowering potted plant of the new variety.

DETAILED BOTANICAL DESCRIPTION

The aforementioned photographs were taken on Apr. 20, 2015 from plants and were approximately 10-11 weeks of age.

The observations and measurements were taken in Andijk, The Netherlands in May 2015 on the same, about 12 week old plants that were cultivated in a greenhouse in 10.5 cm pots.

Color references are made to The Royal Horticultural Society Colour Chart (R.H.S.), 2001.

TABLE 1

DIFFERENCES BETWEEN THE NEW VARIETY 'LOBZ0010' and A MOST SIMILAR VARIETY

| | 'LOBZ0010' | 'KLELE11769', U.S. Plant Pat. No. 24,037, commercially known as 'Curacao Compact White' |
|---|---|---|
| Leaf, shape and margin: | Somewhat wider, serrate, and with a petiole | Narrower, slightly serrate, no petiole |
| Flower, diameter: | Larger: 2.1 cm | Smaller: 1.4 cm |
| Pubescence on leaf and stem: | Little | Very slight |
| Plant habit: | Upright, more compact | Semi-upright, less compact plant |
| | 'LOBZ0010' | Co-applied 'LOBZ0005' |
| Plant habit and size: | Upright | Trailing |

Plant:

*Growth and habit.*—Vigorous growth habit; dense, and freely branching with short internodes, mounding with upright directed stems.

*Height.*—About 10-11 cm (from top of soil).

*Height (inflorescence included).*—About 30 cm.

*Width (horizontal diameter).*—From 25-35 cm.

*Branching characteristics.*—6 main stems, each with 3-4 secondary branches.

*Time to produce a finished flowering plant.*—About 11 weeks for a 12 cm pot.

*Garden performance.*—Used as patio planters, in mixed container plantings, or in garden beds.

*Time to initiate and develop roots.*—21-28 days at 20-23° Centigrade.

Roots:

*Number of days to initiate roots.*—About 15 days at about 22 degrees C.

*Number of days to produce a rooted cutting.*—21-25 days.

*Type.*—Fibrous and freely branching.

*Color.*—RHS N155C.

Foliage:

*Arrangement.*—Alternate.

*Leaf shape.*—Near base: obovate; otherwise oblanceolate, narrow.

*Apex.*—Obtuse.

*Base.*—Attenuate.

*Margin.*—Entire or serrate.

*Leaf length.*—3.5-5.5 cm.

*Leaf width.*—0.6-0.9 cm.

*Immature leaf, color upper surface.*—RHS 137B.

*Immature leaf, color lower surface.*—RHS 138B.

*Mature color upper surface.*—RHS 146B.

*Mature color lower surface.*—RHS 147C.

*Venation type.*—Pinnate.

*Venation color, upper surface.*—Same color as leaf blade.

*Venation color, lower surface.*—A little protruding, same color as leaf blade.

*Texture.*—Weak pubescence, both surfaces.

*Petiole.*—No petiole, leaves are sessile.

Stem:

*Characteristics.*—With slightly strengthened, protruding edges, side branches are developed at almost every node.

*Stem length.*—7-9 cm.

*Diameter.*—0.3-0.5 cm.

*Internode length.*—2.5-3.5 cm.

*Color.*—Mainly RHS 145A.

*Texture.*—Finely pubescent.

Inflorescence:

*Type.*—Raceme, composed of single flowers in an alternate arrangement with one flower per node, subtended by a small leaflet.

*Blooming habit.*—Continuously through the growing season from spring to the fall.

*Quantity of inflorescences per plant.*—About 15 per plant/35 per container.

*Quantity of flowers per inflorescence.*—Up to 16 open flowers, and additional buds.

*Lastingness of individual blooms on the plant.*—3-6 days, depending on temperature.

*Fragrance.*—None.

*Inflorescence length.*—19-22 cm.

Peduncle:

*Color.*—RHS near 143B or 144B.

*Length.*—6-7 cm.

*Diameter.*—0.2 cm.

*Texture.*—Pubescent.

Pedicels:

*Color.*—RHS 147A.

*Length.*—1.3-1.6 cm.

*Diameter.*—0.1 cm.

*Texture.*—Pubescent.

Flower:

*Corolla type and shape.*—Single, zygomorphic; upper lip is formed by two small petals, lower lip has three larger petals; petals are fused at the base forming a relatively long funnel-shaped tube.

Flower bud:

*Shape.*—Elongate.

*Length.*—0.8 cm.

*Diameter.*—0.3-0.4 cm.

*Color (at tight bud).*—RHS 157C (Greenish white) and RHS 157C (White).

Immature flower:

*Main color upper surface.*—RHS 155A.

*Main color lower surface.*—RHS 155C at tip, RHS 155A at base.

*Immature flower, width.*—1.0 cm.

Mature flower:

*Flower, (horizontal) length.*—2.1 cm.

*Flower, (horizontal) width.*—2.1 cm.

*Flower, vertical length (depth).*—2.2 cm.

*Color upper lip, upper surface.*—RHS 155B.

*Color upper lip, lower surface.*—RHS 155B.

*Upper petal lobes, length (from the tube opening):* 1.1-1.2 cm.

*Upper petal lobes, width.*—0.3-0.4 cm.
*Color lower lip, upper surface.*—RHS 155C.
*Color lower lip, lower surface.*—RHS 155C.
*Nectaries at base of lower petals.*—RHS 145D.
*Lower petal lobes, length* (*from the corolla opening*).—1.1-1.4 cm.
*Lower petal lobes, width.*—0.7-1.0 cm.
*Tube, color* (*outside*).—RHS 157B.
*Tube length.*—0.9-1.1 cm.
*Tube width.*—0.3-0.4 cm.

Petal:
*Shape.*—Obovate.
*Apex shape.*—Mucronulate.
*Base.*—Fused, funnel-shape.
*Margin.*—Entire.
*Texture upper surface.*—Glabrous.
*Texture lower surface.*—Short hair, mainly along the mid vein.

Calyx:
*Shape.*—5 sepals in a whorl, slanting outwards, fused at the base.
*Sepal color.*—RHS 138A.
*Sepal length* (*free ends*).—0.8 cm, respective 1.1 cm when including the funnel shaped part.
*Width.*—0.2 cm.
*Shape.*—Ligulate.
*Apex.*—Acute.
*Base.*—Fused.
*Texture.*—Pubescent.

Reproductive organs:
Stamens:
*Quantity.*—5.
*Filament, color.*—RHS 155B.
*Filament length.*—0.6-0.8 cm.
*Filament, diameter.*—0.1 cm.
*Anther color.*—RHS 187A.
*Anther length.*—0.2 cm.
*Pollen amount.*—Little.
*Pollen color.*—RHS 3B to RHS 3C.

Pistil:
*Quantity per flower.*—1.
*Length.*—1.0 cm.
*Stigma color.*—RHS 147A.
*Stigma length.*—0.25 cm.
*Style color.*—RHS 145A.
*Style length.*—From 0.7-0.8 cm.

Fruit and seed set: Occasionally observed outdoors.
Disease and insect resistance: Resistance and susceptibility typical for the species, no special observations made.

The invention claimed is:

1. A new and distinct cultivar of *Lobelia* plant named 'LOBZ0010' as shown and described herein.

* * * * *